(12) United States Patent
Baldo et al.

(10) Patent No.: US 6,486,147 B2
(45) Date of Patent: Nov. 26, 2002

(54) COSMETIC COMPOSITION CONTAINING A STEROID AND A 2-ALKYLALKANOL OR AN ESTER THEREOF

(75) Inventors: France Baldo, Sceaux (FR); Susanne Dreher, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/828,813

(22) Filed: Apr. 10, 2001

(65) Prior Publication Data

US 2001/0044430 A1 Nov. 22, 2001

(30) Foreign Application Priority Data

Apr. 10, 2000 (FR) .............................. 0004576

(51) Int. Cl.⁷ .......................... A61K 31/56; A61K 9/00
(52) U.S. Cl. ..................... 514/178; 424/400; 424/401; 514/844
(58) Field of Search ................. 424/400, 401; 514/178, 844

(56) References Cited

U.S. PATENT DOCUMENTS

| | | | |
|---|---|---|---|
| 4,474,763 A | * 10/1984 | Lubowe | 424/177 |
| 4,496,556 A | * 1/1985 | Orentreich | 514/178 |
| 4,542,129 A | 9/1985 | Orentreich | |
| 4,797,273 A | * 1/1989 | Linn et al. | 424/59 |
| 5,736,537 A | * 4/1998 | Gubernick et al. | 514/178 |
| 5,776,923 A | 7/1998 | Labrie | |
| 5,798,347 A | 8/1998 | Labrie | |
| 5,824,671 A | 10/1998 | Labrie | |
| 5,854,671 A | 12/1998 | Nishi | |
| 5,872,114 A | 2/1999 | Labrie | |
| 5,900,242 A | * 5/1999 | Breton et al. | 424/401 |
| 5,958,946 A | 9/1999 | Styczynski et al. | |

FOREIGN PATENT DOCUMENTS

| | | |
|---|---|---|
| EP | 0 641 557 | 3/1995 |
| EP | 0 646 371 | 4/1995 |
| EP | 0 666 076 | 8/1995 |
| EP | 0 679 388 | 11/1995 |
| EP | 0 705 593 | 4/1996 |
| EP | 0 723 775 | 7/1996 |
| FR | 2 771 105 | 5/1999 |
| JP | 58-170707 | * 10/1983 |
| JP | 06-271468 | 9/1994 |
| JP | Hei 7-196467 | 8/1995 |
| JP | 7-196467 | 8/1995 |
| WO | WO 93/02660 | 2/1993 |
| WO | WO 94/08588 | 4/1994 |
| WO | WO 97/13500 | 4/1997 |

OTHER PUBLICATIONS

Chemical Abstracts, Nakagawa et al., "Solubilizers for Steroids and Steroid Topical Solutions," Database Accession No. 122:89402 CA XP–002156837, Sep. 27, 1994.

Chemical Abstracts, Kitamura et al., "Keratin Formation Promoters for Prevention of Skin Roughness and Aging," Database Accession No. 123:296262 CA XP–002156838, Aug. 1, 1995.

Chemical Abstracts, Hashizume et al., "Melanin Formation Inhibitors Containing Pregnenolones," Database Accession No. 126: 190762 CA XP–002156839, Dec. 24, 1996.

* cited by examiner

*Primary Examiner*—Barbara P. Badio
(74) *Attorney, Agent, or Firm*—Oblon, Spivak, McClelland, Maier & Neustadt, P.C.

(57) ABSTRACT

A composition including at least one steroid chosen from DHEA and/or a biological precursor and/or a chemical or metabolic derivative of the latter, characterized in that it additionally comprises at least one 2-alkylalkanol comprising from 12 to 36 carbon atoms or an ester of such an alcohol. The invention also relates to the cosmetic and dermatological uses of this composition, in particular for preventing or treating chronological or actinic ageing and canities.

42 Claims, No Drawings

COSMETIC COMPOSITION CONTAINING A STEROID AND A 2-ALKYLALKANOL OR AN ESTER THEREOF

BACKGROUND OF THE INVENTION

1. Field of the Invention

The present invention relates to a composition including at least one steroid chosen from DHEA and/or a biological precursor and/or a chemical or metabolic derivative of the latter and at least one 2-alkylalkanol comprising from 12 to 36 carbon atoms or an ester of such an alcohol, to uses of the composition and to a process for dissolving the abovementioned steroid by means of at least one 2-alkylalkanol comprising from 12 to 36 carbon atoms or an ester of such an alcohol.

2. Description of the Background

DHEA or dehydroepiandrosterone is a natural steroid produced essentially by the corticoadrenal glands. Exogenous DHEA, administered topically or orally, is known for its ability to promote keratinization of the epidermis (JP-07 196 467) and to treat dry skin by increasing the endogenous production and the secretion of sebum and by thus strengthening the barrier effect of the skin (U.S. Pat. No. 4,496,556). DHEA is also described for the treatment of the symptoms of the menopause (U.S. Pat. No. 5,854,671) and in the prevention and treatment of osteoporosis (U.S. Pat. No. 5,776,923). The use of DHEA has also been suggested in the treatment of obesity and diabetes (WO 97/13500) or of cardiovascular diseases (U.S. Pat. No. 5,854,671) and in the treatment of some cancers, such as ovarian cancer (U.S. Pat. No. 5,798,347), uterine cancer (U.S. Pat. No. 5,872,114) or breast cancer (U.S. Pat. No. 5,824,671).

In point of fact, DHEA only dissolves with difficulty in aqueous and aqueous/alcoholic media, which limits its formulation in cosmetic or dermatological compositions applied topically or orally. It thus has a tendency to recrystallize or to decompose. The result of this is a loss in effectiveness of these compositions to a greater or lesser extent, depending upon the degree of recrystallization and/or of decomposition, which goes against the desired objective. In addition, this recrystallization or decomposition can modify the overall stability of these compositions and their appearance, which can dissuade the consumer from using them.

Accordingly, the need thus remains to dissolve DHEA, and its precursors and/or derivatives presenting the same recrystallization difficulties, in a physiologically acceptable solubilizing agent.

SUMMARY OF THE INVENTION

The Inventors has now found, surprisingly, that these compounds can be easily dissolved in Guerbet alcohols and esters thereof.

The alcohols referred to as Guerbet alcohols are 2-alkylalkanols corresponding to the following general formula (II):

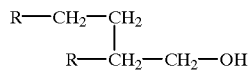

in which R denotes the same saturated aliphatic group.

These alcohols are generally obtained by condensation, at high temperature and in the presence of alkaline catalysts, of two aldehyde molecules to form an aldol, followed by elimination of water. Because of their branched structure, these compounds are liquid at extremely low temperatures. In addition, because of their high molecular weight, they are not very irritating and not very volatile and have good lubricating properties. Finally, their saturated aliphatic chain confers on them very good stability with respect to high temperature oxidation.

These advantageous properties explain why these compounds are currently used in a great many applications and in particular as emollients and conditioning agents in highly varied cosmetic compositions. Some of them have also been disclosed as solubilizing agents for active agents, such as 5-(n-octanoyl)salicylic acid, caffeic acid, kojic acid (EP 0 679 388) and retinol (EP 0 646 371 and EP 0 666 076). However, to the knowledge of the Inventors, the use of Guerbet alcohols for dissolving DHEA, a biological precursor thereof, or a chemical or metabolic derivative thereof has never been described.

Accordingly, the present invention provides a composition including at least one steroid chosen from DHEA and/or a biological precursor and/or a chemical or metabolic derivative of the latter, characterized in that it additionally comprises at least one 2-alkylalkanol comprising from 12 to 36 carbon atoms or an ester of such an alcohol.

Thus, one embodiment of the present invention is a composition, comprising:

(A) at least one steroid selected from the group consisting of DHEA, a biological precursor of DHEA, a chemical derivitive of DHEA, and a metabolic derivative of DHEA, and (B) at least one 2-alkylalkanol comprising from 12 to 36 carbon atoms or an ester thereof.

The present invention also provides a method of preventing or treating chronological or actinic ageing comprising applying the composition of the invention to skin.

The present invention also provides a method of preventing or reducing the papery appearance of the skin, and/or for improving the homogeneity of the color of the skin and/or for lightening the skin and/or reviving the radiance of the complexion, and/or for treating wrinkles and fine lines, and/or for combating cutaneous slackening, and/or for combating or preventing atrophy of the skin, and/or for combating dryness of the skin, comprising applying the composition of the invention to skin.

The present invention also provides a method of cosmetic treating the scalp comprising applying the composition of the invention to the scalp.

The present invention also provides a method of preventing or treating canities comprising applying the composition of the invention to the scalp.

The present invention also provides a method of preparing the composition of the invention by combining (A) and (B).

The present invention also provides a method of preparing the composition the invention by comprising mixing (A) with (B).

The present invention also provides a method of solubilizing a steroid selected from the group consisting of DHEA, a biological precursor of DHEA, a chemical derivitive of DHEA, and a metabolic derivative of DHEA in a composition containing the steroid, comprising incorporating into the composition an amount of at least one 2-alkylalkanol comprising from 12 to 36 carbon atoms or an ester thereof effective to solubilize the steroid in the composition.

The present invention also provides a process for dissolving at least one steroid chosen from DHEA and/or a biological precursor and/or a chemical or metabolic derivative of the latter comprising the stage which consists in mixing the steroid with at least one 2-alkylalkanol comprising from 12 to 36 carbon atoms or with an ester of such an alcohol. The mixing can be carried out under cold conditions, at ambient temperature or under hot conditions, for example at 75° C., generally with stirring.

A more complete appreciation of the invention and many of the attendant advantages thereof will be readily obtained as the same becomes better understood by reference to the following detailed description.

DETAILED DESCRIPTION OF THE INVENTION

According to a preferred embodiment, the process for preparing the composition of the invention additionally comprises the successive stages consisting in: (a) adding, to the mixture obtained above, a composition comprising compounds capable of forming lamellar phases, so as to obtain an oily phase; (b) optionally, mixing this oily phase with an aqueous phase, to prepare an emulsion; (c) subjecting the oily phase obtained according to stage (a) or the emulsion obtained according to stage (b) to a high pressure homogenization, so as to obtain a composition comprising oily globules coated with lamellar phases; and (d) optionally, adding at least one gelling agent to the composition obtained according to stage (c).

This is because the Inventors have discovered that the formation of oily globules coated with lamellar phases, also referred to as "oleosomes", such as disclosed in applications EP-0 641 557 and EP-0 705 593, both incorporated herein by reference, makes it possible to slow down the crystallization of the compositions according to the invention. The compounds capable of forming lamellar phases which can be used for implementing the above process are thus disclosed in particular in the two abovementioned patent applications. They generally comprise the combinations of a lipophilic surfactant, such as a polyol ester, with a hydrophilic surfactant, such as a polyoxyalkylenated polyol ester, and a fatty acid and/or an ionic amphiphilic lipid. The oleosomes generally have a mean diameter of less than 200 nm.

DHEA has the following formula (I):

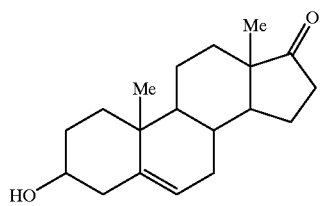

(I)

The DHEA which can be used according to the invention is available from, for example, Akzo Nobel.

The term "biological precursors" of DHEA is refers to compounds which are converted in vivo to DHEA. Particular examples of biological precursors of DHEA include Δ5-pregnenolone, 17α-hydroxypregnenolone and 17α-hydroxypregnenolone sulfate, without this list being limiting.

The term "DHEA derivatives" refers to both the metabolic derivatives and the chemical derivatives of DHEA. Mention may in particular be made, as metabolic derivatives, of Δ5-androstene-3, 17-diol and in particular 5-androstene-3β, 17β-diol, Δ4-androstene-3, 17-dione, 7-hydroxy-DHEA (7α-hydroxy-DHEA or 7β hydroxy-DHEA) and 7-keto-DHEA, which is itself a metabolite of 7β-hydroxy-DHEA, without this list being limiting.

7α-Hydroxy-DHEA is, with 5-androstene-3β, 17β-diol, a major metabolite of DHEA obtained by the action of 7α-hydroxylase on DHEA. 7β-Hydroxy-DHEA is a minor metabolite of DHEA obtained by the action of 7β-hydroxylase on DHEA. The 7-hydroxy-DHEA which can be used in the composition of the invention is preferably 7α-OH-DHEA. A process for the preparation of this compound is described in particular in patent applications FR-2 771 105 and WO 94/08588, both incorporated herein by reference. However, 7β-OH-DHEA is also suitable in the composition according to the present invention.

Mention may in particular be made, as chemical derivatives, of DHEA salts, in particular water-soluble salts, such as DHEA sulfate. Mention may also be made of esters, such as esters of hydroxycarboxylic acids and of DHEA, disclosed in particular in U.S. Pat. No. 5,736,537, incorporated herein by reference, or other esters, such as DHEA salicylate, acetate, valerate (or n-heptanoate) and enanthate. This list is obviously not limiting.

The steroids specifically mentioned above are included within the group of the compounds corresponding to the formula (II):

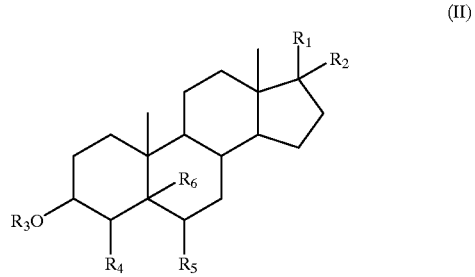

(II)

where $R_1$ represents a hydrogen atom or a hydroxyl group, $R_2$ is a —CO—CH$_3$ radical or a hydroxyl group, or $R_1$ and $R_2$ together form an oxo group, $R_3$ is a hydrogen atom or a —COR' radical, where R' represents a saturated or unsaturated and linear, cyclic or branched $C_1$-$C_{12}$ hydrocarbonaceous radical which is optionally hydroxylated or an aryl radical which is optionally hydroxylated, and either $R_4$ represents a hydrogen atom and $R_5$ and $R_6$ together form a bond, or $R_4$ and $R_5$ together form a bond and $R_6$ represents a hydrogen atom, and their salts.

The term "hydrocarbonaceous radical" is understood to mean, for example, alkyl radicals, such as methyl, ethyl, propyl, isopropyl, n-butyl, isobutyl, sec-butyl, tert-butyl, pentyl, hexyl, heptyl, octyl, nonyl, decyl, undecyl and dodecyl radicals, and alkylene radicals, in particular vinyl or allyl radicals.

The term "aryl radical" is preferably understood to mean the benzyl radical.

The composition according to the present invention includes, as solubilizing agent for the abovementioned steroids, at least one 2-alkylalkanol comprising from 12 to 36 carbon atoms and preferably from 16 to 20 carbon atoms or an ester of such an alcohol. These ranges for the number of carbon atoms include all specific values and subranges therebetween, such as 14, 18, 22, 24, 26, 28, 30, 32, and 34 carbon atoms.

Mention may be made, as 2-alkylalkanols suitable for use in the present invention, of: butyloctanol, pentylnonanol, hexyldecanol, octyldecanol, isostearyl alcohol, octyldodecanol, undecylpentadecanol, dodecylhexadecanol, tetradecyloctadecanol, hexyldecyloctadecanol, decyltetradecanol, tetradecyleicosanol, and cetylarachidol.

All these compounds are commercially available, from Condea Vista under the tradename Isofol®, from Exxon Chemical under the name Exxal© or from Jarchem under the name Jarcol®. Use may also be made of the compound available from Henkel under the tradename Eutanol G. Mention may also be made of the mixture of isocetyl, isostearyl and isoarachidyl alcohols available from Condea under the tradename Isofol 18T®. It is preferable in particular to use 2-octyldodecanol.

Mention may be made, as esters of these alcohols, of an ester of 2-hexyldecanol and of an acid chosen from: palmitic acid, caprylic acid, capric acid, lauric acid, myristic acid and isostearic acid, an ester of 2-butyloctanol and of an acid chosen from thiodipropionic acid and trimellitic acid, 2-decyltetradecyl isostearate, octyldodecyl octanoate and octyldodecyl meadowfoamate, which is an ester of octyldodecanol and of fatty acids derived from *Limnanthes alba* germ oil, available from Fanning Corporation under the tradename Meadowester gme. The acid may have 8 to 18 carbon atoms. This range includes all specific values and subranges therebetween, such as 10, 12, 14, AND 16 carbon atoms.

The concentration of steroids in the composition according to the invention is preferably between 0.001% and 20% by weight, preferably between 0.01 and 10% by weight, more preferably between 0.1 and 3% by weight, with respect to the total weight of the composition. These ranges include all specific values and subranges therebetween, such as 0.002, 0.005, 0.02, 0.05, 0.2, 0.5, 1, 1.5, 2, 2.5, 5, 8, 12, and 15% by weight, with respect to the total weight of the composition.

The amount by weight of 2-alkylalkanol or of an ester thereof is preferably equal to, more preferably is at least twice as great as, the amount by weight of steroids. The amount of 2-alkylalkanol or of an ester thereof advantageously represents from 0.01% to 25%, better still from 1 to 15%, of the total weight of the composition. These ranges include all specific values and subranges therebetween, such as 0.02, 0.05, 0.2, 0.5, 1.5, 2, 2.5, 5, 8, 12, 18, 20, and 22% by weight, with respect to the total weight of the composition.

The composition according to the invention can be provided in any pharmaceutical dosage form normally used for a topical application on the skin, in particular in the form of an oily solution, of an oil-in-water or water-in-oil or multiple emulsion, of a silicone emulsion, of a microemulsion or nanoemulsion, of an oily gel, of a liquid, pasty or solid anhydrous product, or of a dispersion of oil in an aqueous phase in the presence of spherules, it being possible for these spherules to be polymeric nanoparticles, such as nanospheres and nanocapsules, or better still lipid vesicles of ionic and/or nonionic type.

This composition can be more or less fluid and have the appearance of a white or colored cream, of an ointment, of a milk, of a lotion, of a serum, of a paste, of a foam or of a gel. It can optionally be applied to the skin in the form of an aerosol. It can also be provided in the solid form, for example in the form of a stick. It can be used as a product for caring for and/or as a product for making up the skin or as a hair product, for example as a shampoo or conditioner.

As will be readily appreciated by those skilled in the art, the composition of the invention can also comprise the adjuvants customarily used in the cosmetic and dermatological fields, such as hydrophilic or lipophilic gelling agents, hydrophilic or lipophilic active agents, preservatives, antioxidants, solvents, fragrances, fillers, screening agents, pigments, odor absorbers and coloring materials. The amounts of these various adjuvants are those conventionally used in the fields under consideration, for example from 0.01 to 20% of the total weight of the composition. This range includes all specific values and subranges therebetween, such as 0.02, 0.05, 0.1, 0.2, 0.5, 1, 1.5, 2, 2.5, 5, 8, 12, and 15% by weight, with respect to the total weight of the composition.

These adjuvants, depending upon their nature, can be introduced into the fatty phase, into the aqueous phase, into the lipid vesicles and/or into the nanoparticles. These adjuvants and their concentrations must be such that they do not harm the advantageous properties of the steroids according to the invention.

When the composition according to the invention is an emulsion, the proportion of the fatty phase can range from 5 to 80% by weight and preferably from 5 to 50% by weight with respect to the total weight of the composition. These ranges include all specific values and subranges therebetween, such as 10, 15, 20, 25, 35, 40, 60, and 75% by weight with respect to the total weight of the composition. The fatty substances, the emulsifiers and the coemulsifiers used in the composition in the form of an emulsion are chosen from those conventionally used in the field under consideration. The emulsifier and the coemulsifier are preferably present in the composition in a proportion ranging from 0.3 to 30% by weight and preferably from 0.5 to 20% by weight with respect to the total weight of the composition. These ranges include all specific values and subranges therebetween, such as 1, 2, 5, 10, and 25% by weight, with respect to the total weight of the composition.

In addition to solubilizing agents based on 2-alkylalkanols and on their esters, use may be made, as fatty substances which can be used in the invention, of oils and in particular mineral oils (liquid paraffin), oils of vegetable origin (avocado oil, soybean oil), oils of animal origin (lanolin), synthetic oils (perhydrosqualene), silicone oils (cyclomethicone) and fluorinated oils (perfluoropolyethers). Use may also be made, as fatty substances, of fatty alcohols, such as cetyl alcohol, fatty acids, waxes and gums and, in particular, silicone gums.

Mention may be made, as emulsifiers and coemulsifiers which can be used in the invention, of, for example, esters of fatty acid and polyethylene glycol, such as PEG-100 stearate, PEG-50 stearate and PEG-40 stearate; esters of fatty acid and of polyol, such as glyceryl stearate, sorbitan tristearate and the oxyethylenated sorbitan stearates available under the tradenames Tween® 20 or Tween® 60, for example; and mixtures thereof.

Mention may in particular be made, as hydrophilic gelling agents, of carboxyvinyl polymers (carbomer), acrylic copolymers, such as acrylate/alkyl acrylate copolymers, polyacrylamides, polysaccharides, natural gums and clays and mention may be made, as lipophilic gelling agents, of modified clays, such as bentones, metal salts of fatty acids and hydrophobic silica.

Use may in particular be made, as active agents, of depigmenting agents and keratolytic and/or desquamating agents.

In the event of incompatibility, the active agents indicated above and/or the steroids according to the invention can be incorporated in spherules, in particular ionic or nonionic vesicles and/or nanoparticles (nanocapsules and/or nanospheres), so as to isolate them from one another in the composition.

According to an alternative form of the invention, the composition can be adapted to oral administration. In this case, it can be provided in the form of syrups, of suspensions, of solutions or of emulsions.

The composition according to the invention finds an application in particular in the prevention and treatment of signs of chronological or actinic ageing and in the treatment of some pathologies.

The present invention thus also provides for the cosmetic use of the composition mentioned above for preventing or treating chronological or actinic ageing, in particular:

for preventing or reducing the papery appearance of the skin, and/or for improving the homogeneity of the color of the skin and/or for lightening the skin and/or reviving the radiance of the complexion, and/or for treating wrinkles and fine lines, and/or for combating cutaneous slackening, and/or for combating or preventing atrophy of the skin, and/or for combating dryness of the skin.

The present invention also provides for the use of this composition for the cosmetic treatment of the scalp, in particular for preventing or treating canities.

The present invention also relates to the use of the abovementioned composition for manufacturing a preparation intended to tone down pigmentary blemishes.

The present invention also provides for the use of the abovementioned composition for manufacturing a preparation intended for the treatment of canities.

In all of these embodiments, the composition according to the invention and/or the preparation obtained from the latter comprises an effective amount of steroid, sufficient to produce the desired effect, and a physiologically acceptable medium.

The composition can be applied for the desired effect using techniques well-known to those skilled in the art.

EXAMPLES

Having generally described this invention, a further understanding can be obtained by reference to certain specific examples which are provided herein for purposes of illustration only and are not intended to be limiting unless otherwise specified. In these examples, the amounts are shown as percentage by weight, unless otherwise indicated.

Example I

Demonstration of the Solubilizing Effect of Guerbet Alcohols

Three compositions C1 to C3 as defined in Table 1 below are prepared.

TABLE 1

|  | C1 | C2 | C3 | C4 |
|---|---|---|---|---|
| Polyglyceryl (2 mol) distearate | 2% | 2% | 2% | 2% |
| PEG (8 EO) monostearate | 1.35% | 1.35% | 1.35% | 1.35% |
| Stearic acid | 1% | 1% | 1% | 1% |
| Preservatives | 1.35% | 1.35% | 1.35% | 1.35% |
| 2-Octyldodecanol | 0% | 5% | 10% | 20% |
| DHEA | 1% | 1% | 1% | 1% |
| Benzoate of $C_{12-15}$ alcohols | 20% | 15% | 10% | 0% |

TABLE 1-continued

|  | C1 | C2 | C3 | C4 |
|---|---|---|---|---|
| Neutralizing agents | 0.45% | 0.45% | 0.45% | 0.45% |
| Propylene glycol | 10% | 10% | 10% | 10% |
| Gelling agent | 0.5% | 0.5% | 0.5% | 0.5% |
| Water | q.s. for 100% | q.s. for 100% | q.s. for 100% | q.s. for 100% |

The compositions C1 to C3 are prepared in a way which is conventional to a person skilled in the art. The composition C4 is prepared as described in Example 2 below.

After fifteen days at 4° C. or ambient temperature, the composition C1, which is devoid of 2-octyldodecanol (Guerbet alcohol), already includes crystals which are visible under a microscope in polarized light. On the other hand, in compositions C2 to C4, which respectively comprise 5, 10 and 20% by weight of 2-octyldodecanol, the DHEA is completely dissolved, which is reflected by an absence of crystals after two months at 4° C., at ambient temperature, at 37° C. or at 45° C.

It thus clearly emerges from Table 1 that 2-octyldodecanol or another Guerbet alcohol or alcohol ester makes it possible to dissolve DHEA or another steroid.

The solubility of DHEA in various conventional solubilizing agents is mentioned in Table 2 below by way of comparison (the percentage of DHEA is calculated with respect to the total weight of DHEA and of solvent; AT refers to ambient temperature):

TABLE 2

| Solvent | % DHEA | Solubility | Solubility after one month (AT) |
|---|---|---|---|
| Phenoxyethanol | 20% | Soluble at AT | Crystals |
| Propylene glycol | 15–20% | Insoluble at AT | Crystals |
|  | 5–10% | Soluble at 50° C. | Crystals |
| Dodecanol | 10% | Insoluble even at 50° C. | Crystals |
| Benzoate of $C_{12-15}$ alcohols | 3% | Soluble at 50° C. | Crystals |

It emerges from the above Table 2 that DHEA is insoluble in some conventional solvents, such as propylene glycol or dodecanol. In other solvents, such as phenoxyethanol or the benzoate of $C_{12-15}$ alcohols, it is not soluble for a sufficiently long period of time to allow the preparation of commercially viable compositions.

Example 2

|  | Cosmetic Composition |
|---|---|
| Phase A1 |  |
| 2-Octyldodecanol | 20% |
| DHEA | 1% |
| Phase A2 |  |
| Polyglyceryl (2 mol) distearate | 2% |
| PEG (8 EO) monostearate | 1.35% |
| Stearic acid | 1% |
| Preservative | 0.1% |

-continued

| | Cosmetic Composition |
|---|---|
| Phase B | |
| Preservatives | 0.35% |
| Neutralizing agents | 0.25% |
| Propylene glycol | 10% |
| Water | q.s. for 100% |
| Phase C | |
| Gelling agent | 0.5% |
| Neutralizing agent | 0.2% |
| Water | q.s. for 100% |

This composition was prepared in the following way: phases A1, A2 and B were prepared separately by mixing their constituents with stirring under warm conditions. Phases A1 and A2 were mixed under warm conditions and then phase B was added to them. The mixture thus obtained was transferred to a high pressure homogenizer, where it was subjected to three passes at 600 bar before incorporation of phase C.

This composition can be used in twice-daily applications for preventing or treating signs of ageing, such as wrinkles, fine lines, papery appearance of the skin, cutaneous slackening, loss of radiance of the complexion and drying of the skin.

Obviously, numerous modifications and variations of the present invention are possible in light of the above teachings. It is therefore to be understood that within the scope of the appended claims, the invention may be practiced otherwise than as specifically described herein.

This application is based on French patent application serial No. 04576, filed on Apr. 10, 2000, incorporated herein by reference in its entirety.

What is claimed is:

1. A composition, comprising:
   (A) at least one steroid selected from the group consisting of DHEA, a biological precursor of DHEA, a chemical derivative of DHEA, and a metabolic derivative of DHEA, and
   (B) at least one 2-alkylalkanol comprising from 12 to 36 carbon atoms or an ester thereof,
   wherein the biological precursor of DHEA is selected from the group consisting of Δ5-pregnenolone, 17α-hydroxypregnenolone, and 17αhydroxypregnenolone sulfate;
   wherein metabolic derivative of DHEA is selected from the group consisting of Δ5-androstene-3,17-diol, Δ4-androstene- 3,17-dione, 7-hydroxy-DHEA, and 7-keto-DHEA; and
   wherein the chemical derivative of DHEA is selected from the group consisting of DHEA salts and DHEA esters.

2. The composition of claim 1, wherein the steroid is a biological precursor of DHEA selected from the group consisting of Δ5-pregnenolone, 17α- hydroxypregnenolone, and 17α-hydroxypregnenolone sulfate.

3. The composition of claim 1, wherein the steroid is a metabolic derivative of DHEA selected from the group consisting of Δ5-androstene-3,17-diol, Δ4- androstene- 3, 17-dione, 7-hydroxy-DHEA, and 7-keto-DHEA.

4. The composition of claim 1, wherein the steroid is a chemical derivative of DHEA selected from the group consisting of DHEA salts and DHEA esters.

5. The composition of claim 4, wherein the DHEA salt is a water-soluble salt.

6. The composition of claim 4, wherein the DHEA salt is DHEA sulfate.

7. The composition of claim 4, wherein the DHEA ester is selected from the group consisting of esters of hydroxy-carboxylic acids and DHEA, DHEA salicylate, DHEA acetate, DHEA valerate, and DHEA enanthate.

8. The composition of claim 1, which contains from 0.01 to 10% by weight of the steroid with respect to the total weight of the composition.

9. The composition of claim 8, which contains from 0.1 to 3% by weight of the steroid with respect to the total weight of the composition.

10. The composition of claim 1, wherein the 2-alkylalkanol has from 16 to 20 carbon atoms.

11. The composition of claim 10, wherein the 2-alkylalkanol is 2-octyldodecanol.

12. The composition of claim 1, wherein the 2-alkylalkanol is selected from the group consisting of butyloctanol, pentylnonanol, hexyldecanol, octyldecanol, isostearyl alcohol, octyldodecanol, undecylpentadecanol, dodecylhexadecanol, tetradecyloctadeconal, hexyldecyloctdecanol, decyltetradecanol, tetradecyleicosanol, cetylarachidol, a mixture of isocetyl, isostearyl, and isoarachidyl alcohols, and mixtures thereof.

13. The composition of claim 1, wherein the ester of 2-alkylalkanol is (i) an ester of 2-hexyldecanol and of an acid selected from the group consisting of palmitic acid, caprylic acid, capric acid, lauric acid, myristic acid, and isostearic acid, (ii) an ester of 2-butyloctanol and of an acid selected from the group consisting of thiodipropionic acid and trimellitic acid, (iii) 2-decyltetradecyl isostearate, (iv) octyldodecyl octanoate, or (v) octyldodecyl meadowfoamate.

14. The composition of claim 1, which contains an amount aby weight of the 2-alkylalkanol or ester thereof which is at least equal to the equal to the amount by weight of the steroid.

15. The composition of claim 1, which contains from 0.01% to 25% by weight of the 2-alkylalkanol or ester thereof.

16. The composition of claim 15, which contains from 1% to 10% by weight of the 2-alkylalkanol or ester thereof.

17. The composition of claim 1, which is in the form of an oily solution, an oil-in-water emulsion, a water-in-oil emulsionm, a multiple emulsion, a silicone emulsion, a microemulsion, a nanoemulsion, an oily gel, a liquid, pasty or solid anhydrous product, or a dispersion of oil in an aqueous phase in the presence of spherules.

18. The composition of claim 1, which is in the form of a fluid, an ointment, a milk, a lotion, a serum, a paste, a foam, a gel, an aerosol, or a solid.

19. The composition of claim 1, which contains the 2-alkylalkanol.

20. The composition of claim 1, which contain the contains the ester of a 2-alkylalkanol.

21. The composition of claim 1, which further comprises water.

22. The composition of claim 1, wherein the steroid is soluble in the composition.

23. The composition of claim 1, wherein the 2-alkylalkanol is Guerbet alcohol.

24. The composition of claim 1, which contains from 5 to 20% of the 2-alkylalkanol or ester thereof with respect to the total weight of the composition.

25. The composition of claim 1, which contains from 8to 12% of the 2-alkylalkanol or ester thereof with respect to the total weight of the composition.

26. The composition of claim 1, which contains from 1 to 2 by weight of the steroid with respect to the total weight of the composition.

27. The composition of claim 1, wherein the amount by weight of the 2alkylalkanol or ester thereof is greater than or equal to the amount by weight of the steroid.

28. The composition of claim 1, wherein the amount by weight of the 2-alkylalkanol or ester thereof is a least twice as great as the amount by weight of the steroid.

29. The composition of claim 1, wherein the amount by weight of the 2-alkylalkanol or ester thereof is a least five times as great as the amount by weight of the steroid.

30. The composition of claim 1, wherein the amount by weight of the 2-alkylalkanol or ester thereof is at least ten times as great as the amount by weight of the steroid.

31. The composition of claim 1, wherein the steroid is DHEA.

32. The composition of claim 1, wherein the steroid is 7-hydroxy-DHEA.

33. The composition of claim 1, wherein the steroid is 7-keto-DHEA.

34. A method of treating chronological or actinic ageing comprising applying the composition or claim 1 to skin.

35. A method of preventing or treating signs of chronological or actinic ageing comprising appling the composition of claim 1 to skin.

36. A method of preventing or reducing the papery appearance of the skin, and/or for improving the homogeneity of the color of the skin and/or for lightening the skin and/or reviving the radiance of the complexion, and/or for treating wrinkles and fine lines, and/or for combating cutaneous slackening, and/or for combating or preventing atrophy of the skin, and/or for combating dryness of the skin, comprising applying the composition of claim 1 to skin.

37. A method of cosmetic treating the scalp comprising applying the composition of claim 1 to the scalp.

38. A method of preventing or treating canities comprising applying the composition of claim 1 to the scalp.

39. A method of preparing the composition of claim 1, comprising combining (A) and (B).

40. The method of claim 39, further comprising in succession:

(a) adding, to the mixture of the steroid and of the 2-alkylalkanol, a composition comprising compounds capable of forming lamellar phases, so as to obtain an oily phase;

(b) optionally, mixing this oily phase with an aqueous phase, to prepare an emulsion;

(c) subjecting the oily phase obtained from (a) or the emulsion obtained from (b) to a high pressure homogenization, so as to obtain a composition comprising oily globules coated with lamellar phases; and (d) optionally, adding at least one gelling agent to the composition obtained from (c).

41. A method of preparing the composition of claim 1, comprising mixing (A) with (B).

42. A method of solubilizing a steroid selected form the group consisting of DHEA, a biological precursor of DHEA, a chemical derivative of DHEA, and a metabolic derivative of DHEA in a composition containing the steroid, comprising incorporating into the composition an amount of at least one 2-alkylalkanol comprising from 12 to 36 carbon atoms or an ester thereof effective to solubilize the steroid in the composition, wherein the biological precursor of DHEA is selected from the group consisting of Δ5-pregnenolone, 17α-hydroxypregnenolone, and 17α-hydroxypregnenolone sulfate;

wherein the metabolic derivative of DHEA is selected from the group consisting of Δ5-androstene-3,17-diol, Δ4-androstene- 3,17-dione, 7-hydroxy-DHEA, and 7-keto-DHEA; and wherein the chemical derivative of DHEA is selected from the group consisting of DHEA salt and DHEA ester.

* * * * *

UNITED STATES PATENT AND TRADEMARK OFFICE
CERTIFICATE OF CORRECTION

PATENT NO. : 6,486,147 B2  
DATED : November 26, 2002  
INVENTOR(S) : Baldo et al.

It is certified that error appears in the above-identified patent and that said Letters Patent is hereby corrected as shown below:

<u>Title page,</u>  
Item [75], Inventors, "France Baldo" should read -- Francine Baldo --.

<u>Column 9,</u>  
Line 48, "17αhydroxypregnenolone" should read -- 17α-hydroxypregnenolone --.

<u>Column 10,</u>  
Line 23, "hexyldecyloctdecanol" should read -- hexyldecyloctadecanol --;  
Line 35, "aby" should read -- by --;  
Line 36, "at least equal to the equal to" should read -- at least equal to the --;  
Line 45, "emulsionm" should read -- emulsion --;  
Line 54, "which contain the contains" should read -- which contains --; and  
Line 65, "8to" should read -- 8 to --.

<u>Column 11,</u>  
Lines 1-2, "from 1to2by" should read -- from 1 to 2% by --;  
Line 5, "2alkylalkanol" should read -- 2-alkylalkanol --;  
Line 11, "a least" should read -- at least --;  
Line 22, "of treating" should read -- of preventing or treating --;  
Line 23, "or" should read -- of --; and  
Line 25, "appling" should read -- applying --.

<u>Column 12,</u>  
Line 37, "salt" should read -- salts --; and  
Line 38, "ester" should read -- esters --.

Signed and Sealed this

Thirteenth Day of May, 2003

JAMES E. ROGAN  
*Director of the United States Patent and Trademark Office*